United States Patent
Blanc

(10) Patent No.: US 10,682,174 B2
(45) Date of Patent: Jun. 16, 2020

(54) DEVICE FOR RESECTING AN ORGAN IN A CAVITY OF A BODY

(71) Applicant: AB MEDICA, Mery-sur-Cher (FR)

(72) Inventor: Alexandre Blanc, Marseilles (FR)

(73) Assignee: AB MEDICA, Mery-sur-Cher (FR)

( * ) Notice: Subject to any disclaimer, the term of this patent is extended or adjusted under 35 U.S.C. 154(b) by 316 days.

(21) Appl. No.: 15/575,002

(22) PCT Filed: May 18, 2016

(86) PCT No.: PCT/FR2016/000087
§ 371 (c)(1),
(2) Date: Nov. 17, 2017

(87) PCT Pub. No.: WO2016/185102
PCT Pub. Date: Nov. 24, 2016

(65) Prior Publication Data
US 2018/0140351 A1 May 24, 2018

(30) Foreign Application Priority Data
May 20, 2015 (FR) ..................................... 15 01040

(51) Int. Cl.
*A61B 18/14* (2006.01)
*A61B 1/00* (2006.01)
*A61B 18/00* (2006.01)

(52) U.S. Cl.
CPC ........ *A61B 18/149* (2013.01); *A61B 1/00124* (2013.01); *A61B 2018/00172* (2013.01)

(58) Field of Classification Search
CPC ... A61B 1/018; A61B 1/00119; A61B 1/0008; A61B 1/0011; A61B 1/00135;
(Continued)

(56) References Cited

U.S. PATENT DOCUMENTS 3,752,159 A * 8/1973 Wappler ................. A61B 17/32
606/46
3,835,842 A * 9/1974 Iglesias .................... A61B 1/30
606/46
(Continued)

FOREIGN PATENT DOCUMENTS

CA 989215 A 5/1976
CN 201529144 U 7/2010
(Continued)

OTHER PUBLICATIONS

International Search Report, dated Aug. 17, 2016, from corresponding PCT application No. PCT/FR2016/000087.

*Primary Examiner* — Michael F Peffley
(74) *Attorney, Agent, or Firm* — Young & Thompson

(57) ABSTRACT

Disclosed is a device for resecting an organ in a cavity of a living body. The device includes a guide with a tube and a tube, both cylindrical, the tube being mounted in the first tube; an electrical conductor surrounded by an electrically insulating sheath, the tube being a cylinder of revolution with an inner radius of value R1, the tube including a part which is a cylinder of revolution with an outer radius of value R2<R1 and with an angle at the center of a value Ac, and a part which is not a cylinder of revolution and has an angle at the center of value "360°–Ac"; the insulated conductor contacts the part of the tube, between the outer and inner walls of this tube; and a unit for keeping this insulated conductor in contact with the part of the tube.

20 Claims, 1 Drawing Sheet

Figure 1:
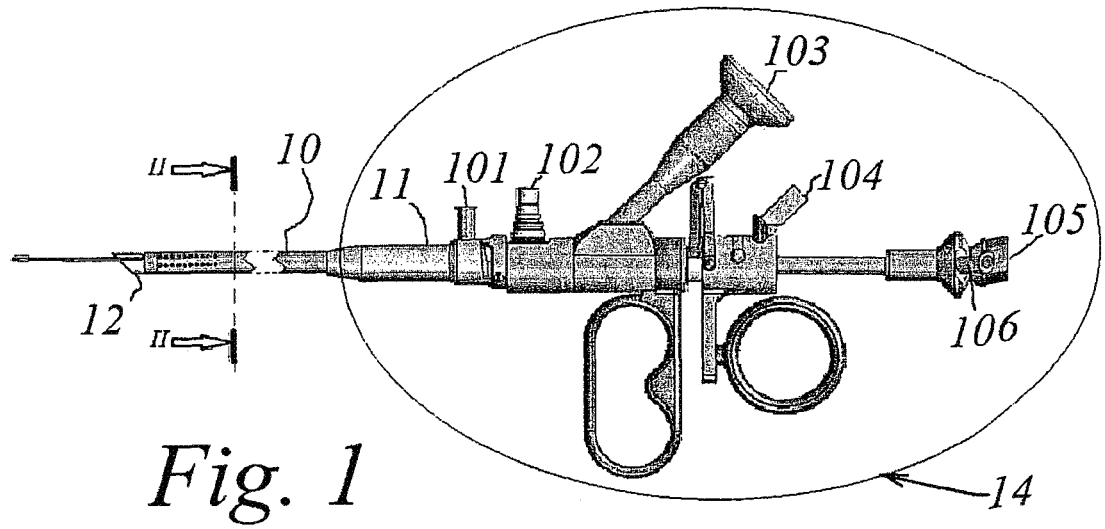

(58) Field of Classification Search
CPC ... A61B 1/00154; A61B 1/0057; A61B 1/012; A61B 1/00124; A61B 1/00071
See application file for complete search history.

(56) References Cited

U.S. PATENT DOCUMENTS

| | | | |
|---|---|---|---|
| 4,024,869 A | | 5/1977 | Bonnet |
| 5,807,240 A | * | 9/1998 | Muller et al. ............ A61B 1/30 600/135 |
| 6,358,200 B1 | * | 3/2002 | Grossi ...................... A61B 1/12 600/156 |
| 6,730,081 B1 | | 5/2004 | Desai |
| 2015/0351826 A1 | | 12/2015 | Kroeber et al. |

FOREIGN PATENT DOCUMENTS

| | | |
|---|---|---|
| DE | 27 46 983 A1 | 5/1978 |
| DE | 10 2009 025 047 A1 | 8/2011 |
| FR | 2 294 679 A1 | 7/1976 |
| WO | 2014/114600 A1 | 7/2014 |

\* cited by examiner

DEVICE FOR RESECTING AN ORGAN IN A CAVITY OF A BODY

The present invention relates to devices for performing resection of all or part of an organ situated in a cavity of a living body, in particular of a human being, regardless of the nature of the organ, and regardless of whether it is healthy or not healthy, and more particularly the invention relates to devices known in the art under the term "resectoscopes".

Such devices are described and illustrated by way of example in patent applications WO 2014/114600, DE 10 2009 025 047, CN 201529144, and in particular U.S. Pat. No. 6,358,200.

Such a known device essentially comprises: a guide defined between a proximal end and a distal end, the guide comprising a through duct that is open at both of its ends; two electrically conductive wires that are externally insulated and slidably mounted in the duct, each of the two wires having a first end and a second end, which ends are suitable, when the wires move in translation in the duct, for emerging respectively from the proximal end and from the distal end of the duct, the first ends of the two wires having means for connection to two poles of an electrical power supply; an open loop defined between two free terminals and made of an electrically conductive resistive material so as to produce heat by the Joule effect and thus enable all or part of a determined organ to be ablated by burning; and means for electrically connecting the two free terminals of the open loop respectively to the two second ends of the two conductive wires.

Inside the guide, tubes are also provided that serve, by way of example, for passing surgical instruments or the like, for introducing or for insufflating various fluids, in particular gaseous fluids, into the cavity, for sucking out any element present in the cavity, etc.

The guide that is to be introduced into the cavity (or lumen) in which it is to perform resection must also present a transverse dimension that is as small as possible and have an outer shell that is easy to obtain both industrially and commercially, and it must also be able to contain a non-negligible number of tubes and elements that are essential for performing resection, and possibly for performing surgical operations other than resection.

Thus, an object of the present invention is to provide a device as defined above for performing resection of all or part of an organ in a cavity of a living body, in particular of a human being, that satisfies the above-mentioned requirements and that is easy to make industrially.

More precisely, the present invention provides a device for performing resection of an organ in a cavity of a living body, in particular of a human being, the device being known under the term "resectoscope", and comprising at least: a guide defined between a proximal end and a distal end, said guide defining a duct that is open at both its proximal end and at its distal end, said guide being constituted at least by a first cylindrical tube and by a second cylindrical tube, the second tube being mounted in the first tube, at least one electrical conductor surrounded by a sheath made of electrically insulating material, said electrical conductor as insulated in this way being mounted in said duct, and inlet/outlet means mounted in cooperation with the proximal end of said guide, the device being characterized by the facts that said first tube is a cylinder of revolution having an inside radius of value R1, said second tube comprises: a first portion, being a portion of a cylinder of revolution having an angle at the center of value Ac and having an outside radius of value R2, where R2 is less than R1, and a second portion that is a portion of a cylinder that is not a portion of a cylinder of revolution and that has an angle at the center of value "360°−Ac", the two edges of the second portion of the second tube being in continuity respectively with the two edges of the first portion of the second tube, and said insulated conductor is mounted in contact on said second portion of said second tube between the outside wall of the second tube and the inside wall of the first tube, and that it further includes means for holding said insulated conductor in contact on said second portion of the second tube.

Figure 2:
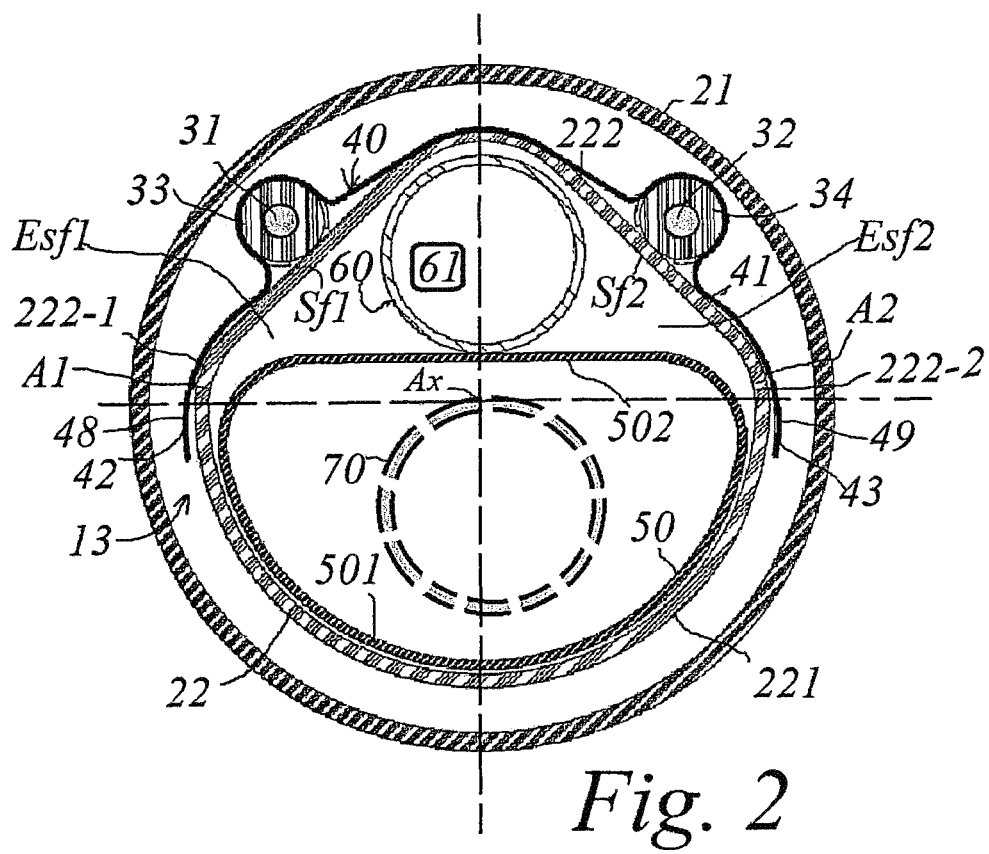

Other characteristics and advantages of the present invention appear from the following description given with reference to the accompanying drawings by way of non-limiting illustration, in which:

FIG. 1 is a general side view of a device of the invention for performing resection of all or part of an organ in a cavity of a living body, in particular of a human being, the device including a guide and inlet/outlet means mounted in association with the guide; and FIG. 2 is a section view of an embodiment of the guide used in the structure of the device of the invention.

It is specified that, in the present description, if the adverb "substantially" is associated with a qualification to any given means, the qualification may be understood equally well as meaning approximately or exactly.

The present invention relates to a device for performing resection of an organ in a cavity of a living body, in particular of a human being, by burning, which device finds a particularly advantageous application in the field of hysteroscopy for intra-uterine surgery. Such a device, known to practitioners under the term "resectoscope", enables intra-uterine interventions to be performed to ablate all or part of an organ, e.g. a polyp, a tumor, a synechia, a uterine malformation, or the like.

With reference to the two accompanying figures, the device comprises at least a guide 10 defined between a proximal end 11 and a distal end 12, the guide defining a duct that is open at both its proximal end and at its distal end, the guide being constituted at least by a first cylindrical tube 21 and by a second cylindrical tube 22, the second tube 22 being mounted in the first tube 21, at least one electrical conductor surrounded by a sheath 33, 34 made of an electrically insulating material, the electrical conductor 31, 32 as insulated in this way being mounted in the duct 13, and inlet/outlet means 14 mounted in cooperation with the proximal end 11 of the guide 10.

According to an essential characteristic of the invention, The first tube 21 is a cylinder of revolution having an inside radius of value R1, while the second tube 22 has a first portion 221 being a portion of a cylinder of revolution having an angle at the center having a value Ac, e.g. substantially 180°, as shown, and an outside radius of value R2 that is less than R1, and a second portion 222 that is not a portion of a cylinder of revolution and that has an angle at the center of value "360°−Ac", the two edges 222-1 and 222-2 of the second portion 222 of the second tube 22 being in continuity respectively with the two edges of the first portion 221 of the second tube 22.

To facilitate the present description, the above defined tube 21 is always referred to as the tube that is a "cylinder of revolution". However it should be understood, in the meaning of the present description, this terminology covers both a tube that is a cylinder of revolution in the true mathematical meaning of the term, and a tube that can be considered, at least functionally, as being a cylinder of revolution.

Also, as shown in FIG. 2, the at least one insulated conductor 31, 32 is mounted in contact on the second portion 222 of the second tube 22 between the outside wall of the second tube and the inside wall of the first tube 21, and the device includes means 40 for holding the at least one insulated conductor 31, 32 in contact on the second portion 222 of the second tube 22.

According to a preferred characteristic of the invention, the means 40 for holding the second conductor 31, 32 in contact on the second portion 222 of the second tube 22, which contact need not necessarily be stationary but could be slidable along the longitudinal axis, are themselves constituted by a clip 41 made of relatively resilient metal material, such as a pre-formed plate made of a material such as stainless steel. The clip then has two lateral longitudinal edges 48, 49, each in the form of a re-entrant resilient hook 42, 43 (i.e. presenting a shape that is substantially concave). These two re-entrant resilient hooks are clipped by passing resiliently over the two connection edges A1, A2 formed respectively between the first portion 221 of the second tube 22 and its second portion 222, and by wrapping at least in part around these two edges, the at least one insulated conductor 31, 32 being clamped relatively between the clip 41 and the second portion 222 of the second tube 22, FIG. 2.

In a preferred embodiment, the second portion 222 of the second tube 22 presents at least one substantially plane surface Sf1, Sf2 facing the inside wall of the first tube 21. This plane surface can be obtained easily, either from a conventional tube that is a cylinder of revolution, by flattening a portion of its wall, or else directly by profiling.

Advantageously, in order to satisfy nearly all possible uses of the device, the second portion 222 of the second tube 22 presents two substantially plane surfaces Sf1, Sf2 facing the inside wall of the first tube, which two surfaces Sf1, Sf2 make between them an angle lying between 0° to 180° (bounds not included) and are inscribed in the surface of revolution defined by the outside surface of the first portion 221 of the second tube 22. In still more advantageous manner, the two substantially plane surfaces Sf1, Sf2 make between them an angle that is substantially equal to 90°, FIG. 2.

Under such circumstances, the device can then most advantageously include two insulated conductors 31, 32 held in contact respectively on each of the two substantially plane surfaces Sf1, Sf2, while using the same clip 41 as described above.

In the above-described configuration, the device can also advantageously include a third cylindrical tube 50, this third tube having a first portion 501 that is a cylinder of revolution with an angle at the center having a value substantially equal to 180° and an outside radius of value R3 substantially equal to the value of the radius of the cylindrical inside surface of revolution of the first portion 221 of the second tube 22, and a second portion 502 that is substantially plane, the two edges of this second portion of the third tube being in continuity respectively with the two edges of the first portion 501 of this third tube, the third tube 50 being arranged inside the second tube 22 in such a manner that its first portion 501 is substantially congruent and in correspondence with the inside surface of the first portion 221 of the second tube 22, as shown in FIG. 2.

In an embodiment that is possible with the above-described configuration, the device may then advantageously further include a fourth cylindrical tube 60 that is optionally a cylinder of revolution, situated in the space of 61 defined between the substantially plane second portion 502 of the third tube 50 and the two plane surfaces Sf1, Sf2 of the second tube 22.

In certain applications, it is also advantageous to provide a fifth tube 70, shown in dashed lines in FIG. 2, mounted in the third tube 50.

In an embodiment that is preferred, industrially speaking, the first tube 21, the first portion 221 of the second tube 22, and the first portion 501 of the third tube 50, all three of which are in the shape of cylinders of revolution, share a substantially common axis Ax, FIG. 2.

The above-mentioned inlet/outlet means 14 as shown in FIG. 1 are known in the prior art and are mounted in fluid flow or mechanical connection with the various tubes and elements that are defined above.

Thus, with the device of the invention an embodiment of which is shown in FIGS. 1 and 2:

the space between the first tube 21 and the second tube 22 is used to perform suction during surgical intervention, this suction having an outlet via the extraction opening 101;

in order for the scene of the operation inside the lumen to be visible, it is necessary to have lighting at the distal outlet 12 of the guide 10. In advantageous and known manner, this lighting is provided by a bundle of optical fibers mounted in cooperation with a light source (not shown in figures). This bundle is situated in the space comprising two portions Esf1, Esf2 as defined by the second tube 22, the third tube 50, and the fourth tube 60. This bundle of optical fibers is generally constituted as two branches situated on either side of the fourth tube 60, essentially in the two portions Esf1 and Esf2, and emerging via the outlet opening 102;

as in any intervention, in order to be able to observe during the operation, it is necessary to introduce an endoscopic camera. This introduction takes place via the inlet eyepiece 103 that is connected to the fourth tube 60, the camera going along the inside of the fourth tube 60 in order to emerge at the distal end 12 of the guide 10. However, it should be observed that instead of an endoscopic camera, it is possible to arrange optical elements, lenses, waveguides, etc. in the tube 60 in order to transmit images of the scene of the operation, with the camera being installed solely in cooperation with the inlet eyepiece 103;

as mentioned above in the introduction, such a device makes it possible to perform resections by cutting off bodies, such as polyps, situated in a lumen, by using a resistance that is heated by the Joule effect. Under such circumstances, the electrical conductors 31, 32 and possibly the first tube 21 are suitable for connecting to an electrical power supply. The ends of the two conductors 31, 32 are situated at the electrical connector 104;

when it is necessary to use specific instruments other than those for resection, these instruments are introduced to the field of the operation via the inlet 105 of the device, which includes the fifth tube 70 mounted in cooperation with this inlet and lying on the axis Ax of the guide 10, thereby facilitating introducing these instruments, which are generally relatively rigid, and which can therefore be introduced and moved in sliding along a straight line only;

the inside of the third tube 50 is used, during the surgical intervention, for delivering an irrigation fluid that is introduced via the inlet 106 and that is sucked out together with the waste generated by the operation via the space connected to the above defined outlet 101 (FIG. 1).

Finally, it is mentioned that the tubes 21, 22, 50, and 60 are advantageously made of stainless steel, that the insulated electrical conductors 31, 32 are generally made of a material that is a good conductor of electricity, such as copper, and that the insulating material out of which the sheaths 33, 34 are made is polytetrafluoroethylene (PTFE), for example.

The way the above-described device is used is itself well known. It is not described in greater detail herein for the reason of simplifying the present description, particularly since this use does not come within the field protected by the invention.

It is nevertheless emphasized that, by virtue of its structure, the device of the invention as described above is very compact, occupying little space transversely, while providing practitioners with a maximum of options in use, even for surgical interventions in cavities for which access is relatively narrow and difficult.

The invention claimed is:

1. A device for performing resection of an organ in a cavity of a living body, said device comprising:
    a guide defined between a proximal end and a distal end, said guide defining a duct that is open at both its proximal end and its distal end, said guide comprising at least a first cylindrical tube and a second cylindrical tube, the second tube being mounted within the first tube;
    at least one insulated conductor comprising an electrical conductor surrounded by a sheath made of electrically insulating material, said insulated conductor being mounted in said duct; and
    an inlet/outlet mounted in cooperation with the proximal end of said guide; wherein:
    said first tube is a cylinder of revolution having an inside radius of value R1;
    said second tube comprises:
        a first portion, being a portion of a cylinder of revolution having a central angle defined between two edges of the first portion and a center thereof, wherein said central angle of the first portion has a value Ac, and said first portion has an outside radius of value R2, where R2 is less than R1; and
        a second portion that is a portion of a cylinder that is not a cylinder of revolution, wherein said second portion has a central angle defined between two edges of the second portion and a center thereof, said central angle of the second portion having a value of (360°−Ac),
        the two edges of the second portion of the second tube being in continuity respectively with the two edges of the first portion of the second tube;
    wherein:
        said insulated conductor is mounted in contact on said second portion of said second tube between an outside wall of the second tube and an inside wall of the first tube; and
        said device further comprises a holder that holds said insulated conductor in contact on said second portion of the second tube.

2. A device according to claim 1, wherein the holder that holds said insulated conductor in contact on the second portion of the second tube is a clip having two lateral longitudinal edges, each of the two lateral longitudinal edges is re-entrant resilient hook, the two re-entrant resilient hooks being clipped by going over two connection edges formed respectively between the first portion of the second tube and its second portion, and wrapping at least in part around the two connection edges, said insulated conductor being positioned between the clip and said second portion of the second tube.

3. A device according to claim 1, wherein said second portion of the second tube presents at least one substantially plane surface facing the inside wall of the first tube.

4. A device according to claim 3, wherein said second portion of the second tube presents two substantially plane surfaces facing the inside wall of the first tube, these two plane surfaces forming between them an angle, θ, where 0°<θ<180°, and the angle, θ, is inscribed in the surface of revolution defined by an outside surface of the first portion of the second tube.

5. A device according to claim 4, wherein the two substantially plane surfaces make between them an angle that is substantially equal to 90°.

6. A device according to claim 4, wherein said at least one insulated conductor comprises two insulated conductors held by said clip in contact respectively on each of the two substantially plane surfaces.

7. A device according to claim 5, further comprising a third cylindrical tube, said third tube comprising:
    a first portion forming a portion of a cylinder of revolution with an angle at the center having a value substantially equal to 180° and an outside radius of value R3 substantially equal to the value of the radius of a cylindrical inside surface of revolution of the first portion of the second tube;
    a substantially plane second portion, the two edges of the second portion of the third tube being in continuity respectively with the two edges of said first portion of said third tube; and
    said third tube being arranged inside the second tube in such a manner that its first portion is substantially congruent and in correspondence with the inside surface of the first portion of the second tube.

8. A device according to claim 7, further comprising a fourth cylindrical tube situated in the space defined between the substantially plane second portion of the third tube and the two plane surfaces of the second tube.

9. A device according to claim 7, further comprising a fifth tube mounted in said third tube.

10. A device according to claim 7, wherein said first tube, the first portion of the second tube, and the first portion of the third tube, all three of which are in the shape of portions of cylinders of revolution, share a substantially common axis (Ax).

11. A device according to claim 2, wherein said second portion of the second tube presents at least one substantially plane surface facing the inside wall of the first tube.

12. A device according to claim 11, wherein said second portion of the second tube presents two substantially plane surfaces facing the inside wall of the first tube, these two plane surfaces forming between them an angle, θ, where 0°<θ<180°, and the angle, θ, is inscribed in the surface of revolution defined by an outside surface of the first portion of the second tube.

13. A device according to claim 12, wherein the two substantially plane surfaces make between them an angle that is substantially equal to 90°.

14. A device according to claim 5, wherein said at least one insulated conductor comprises two insulated conductors held by said clip in contact respectively on each of the two substantially plane surfaces.

15. The device of claim 8, wherein the fourth cylindrical tube defines a cylinder of revolution.

16. A device according to claim 1, further comprising a third cylindrical tube, said third tube comprising:
    a first portion forming a portion of a cylinder of revolution with an angle at the center having a value substantially equal to 180° and an outside radius of value R3 substantially equal to the value of the radius of a cylindrical inside surface of revolution of the first portion of the second tube;

a substantially plane second portion, the two edges of the second portion of the third tube being in continuity respectively with the two edges of said first portion of said third tube; and said third tube being arranged inside the second tube in such a manner that its first portion is substantially congruent and in correspondence with the cylindrical inside surface of the first portion of the second tube.

17. A device according to claim 2, further comprising a third cylindrical tube, said third tube comprising:

a first portion forming a portion of a cylinder of revolution with an angle at the center having a value substantially equal to 180° and an outside radius of value R3 substantially equal to the value of the radius of a cylindrical inside surface of revolution of the first portion of the second tube;

a substantially plane second portion, the two edges of the second portion of the third tube being in continuity respectively with the two edges of said first portion of said third tube; and said third tube being arranged inside the second tube in such a manner that its first portion is substantially congruent and in correspondence with the cylindrical inside surface of the first portion of the second tube.

18. A device according to claim 3, further comprising a third cylindrical tube, said third tube comprising:

a first portion forming a portion of a cylinder of revolution with an angle at the center having a value substantially equal to 180° and an outside radius of value R3 substantially equal to the value of the radius of a cylindrical inside surface of revolution of the first portion of the second tube;

a substantially plane second portion, the two edges of the second portion of the third tube being in continuity respectively with the two edges of said first portion of said third tube; and said third tube being arranged inside the second tube in such a manner that its first portion is substantially congruent and in correspondence with the cylindrical inside surface of the first portion of the second tube.

19. A device according to claim 4, further comprising a third cylindrical tube, said third tube comprising:

a first portion forming a portion of a cylinder of revolution with an angle at the center having a value substantially equal to 180° and an outside radius of value R3 substantially equal to the value of the radius of a cylindrical inside surface of revolution of the first portion of the second tube;

a substantially plane second portion, the two edges of the second portion of the third tube being in continuity respectively with the two edges of said first portion of said third tube; and said third tube being arranged inside the second tube in such a manner that its first portion is substantially congruent and in correspondence with the cylindrical inside surface of the first portion of the second tube.

20. A device according to claim 6, further comprising a third cylindrical tube, said third tube comprising:

a first portion forming a portion of a cylinder of revolution with an angle at the center having a value substantially equal to 180° and an outside radius of value R3 substantially equal to the value of the radius of a cylindrical inside surface of revolution of the first portion of the second tube;

a substantially plane second portion, the two edges of the second portion of the third tube being in continuity respectively with the two edges of said first portion of said third tube; and said third tube being arranged inside the second tube in such a manner that its first portion is substantially congruent and in correspondence with the cylindrical inside surface of the first portion of the second tube.

\* \* \* \* \*